(12) United States Patent
Madon et al.

(10) Patent No.: US 9,006,129 B2
(45) Date of Patent: Apr. 14, 2015

(54) ETHYNYLATION CATALYST AND METHOD OF MAKING SAME

(71) Applicant: BASF Corporation, Florham Park, NJ (US)

(72) Inventors: Rostam Madon, Flemington, NJ (US); Peter Nagel, Highlands, NJ (US); Scott Hedrick, Solon, OH (US); Deepak Thakur, Solon, OH (US)

(73) Assignee: BASF Corporation, Florham Park, NJ (US)

( * ) Notice: Subject to any disclaimer, the term of this patent is extended or adjusted under 35 U.S.C. 154(b) by 0 days.

(21) Appl. No.: 14/203,664

(22) Filed: Mar. 11, 2014

(65) Prior Publication Data

US 2014/0275639 A1    Sep. 18, 2014

Related U.S. Application Data

(60) Provisional application No. 61/788,851, filed on Mar. 15, 2013.

(51) Int. Cl.
  *B01J 23/72*    (2006.01)
  *B01J 23/843*   (2006.01)
  *C07C 29/42*    (2006.01)

(52) U.S. Cl.
  CPC .............. *B01J 23/72* (2013.01); *B01J 23/8437* (2013.01); *C07C 29/42* (2013.01)

(58) Field of Classification Search
  USPC .................... 568/874; 564/855, 874; 502/244
  See application file for complete search history.

(56) References Cited

U.S. PATENT DOCUMENTS

| | | | |
|---|---|---|---|
| 2,939,844 A | | 6/1960 | Ellinger et al. |
| 3,920,759 A | * | 11/1975 | Hort ............................ 568/855 |
| 3,954,669 A | | 5/1976 | Broecker et al. |
| 3,957,888 A | | 5/1976 | Reiss et al. |
| 4,067,914 A | | 1/1978 | Reiss et al. |
| 4,093,668 A | | 6/1978 | Reiss et al. |
| 4,127,734 A | | 11/1978 | Fremont |

FOREIGN PATENT DOCUMENTS

| | | | |
|---|---|---|---|
| CN | 102658158 A | 9/2012 | |
| DE | 102009010158 A1 * | 9/2010 | ............... B01J 23/89 |
| WO | 2010119448 A1 | 10/2010 | |

OTHER PUBLICATIONS

English Language Abstract of CN102658158 Sep. 12, 2012.
English Language Abstract of WO 2010-119448 Oct. 21, 2010.
International Search Report dated Jun. 23, 2014.

* cited by examiner

*Primary Examiner* — Kamal Saeed
*Assistant Examiner* — Janet L Coppins
(74) *Attorney, Agent, or Firm* — Elizabeth Pietrowski

(57) ABSTRACT

A novel catalyst useful in the ethynylation of formaldehyde to butynediol is formed by precipitating copper and bismuth from a salt solution of such metals, utilizing an alkali metal hydroxide as the precipitating agent to deposit copper and bismuth hydroxide as a coating around a siliceous carrier particle.

20 Claims, 1 Drawing Sheet

ETHYNYLATION CATALYST AND METHOD OF MAKING SAME

FIELD OF THE INVENTION

The present invention is directed to a novel catalyst and method of preparing same for use in the catalytic ethynylation of formaldehyde, known as the Reppe reaction.

BACKGROUND OF THE INVENTION

Since the time of publication of German Pat. No. 725,326, various catalysts have been disclosed for the synthesis of butynediol from formaldehyde and acetylene, known as the Reppe ethynylation reaction. Suitable catalysts have proved to be acetylides of heavy metals, especially copper, which can be obtained from reacting acetylene with the suitable heavy metal compound. In a broader sense, the heavy metal compounds are also described as catalysts because of the fact that the actual catalyst, that is to say the acetylide of the heavy metal, is formed directly on passing acetylene into a suitable reaction mixture which contains the heavy metal compound as a "catalyst precursor" and therefore as a rule the manufacture of the catalyst merely entails manufacturing a suitable heavy metal compound. Accordingly, the use of a particular heavy metal compound of this type is regarded as the actual invention in the text, which follows.

Copper compounds are known to be particularly suitable heavy metal compounds for the above purpose; they include, copper carbonate, copper phosphate, copper formate, copper acetate, copper-(II) chloride, copper-(I) chloride, ammoniacal copper sulfate, copper silicate and copper oxide. These compounds can be used unsupported or may be supported on carriers.

In order to suppress formation of the by-product cuprene during the synthesis of butynediol, additives such as bismuth oxide, bismuth oxyiodide, mercury oxide, mercury iodide, selenium-sulfur, potassium iodide, copper iodide, silver iodide, lead iodide, cerium oxide and selenium dioxide are used (cf. German Pat. No. 740,514 and U.S. Pat. No. 2,300,969).

E. V. Hort (GAF Corporation) U.S. Pat. No. 3,920,759 (1975), discloses a process patent for making butynediol using a copper oxide containing catalyst precursor with about 5 to about 20% copper, 0 to about 3% bismuth, and a magnesium silicate carrier. Importantly, the Hort patent teaches that the catalyst is prepared via impregnation of the magnesium silicate support with a solution of $Cu(NO_3)_2.3H_2O$ and $Bi(NO_3)_3.5H_2O$.

According to U.S. Pat. No. 3,920,759, the synthesis is carried out with the catalyst, impregnated on an inert powdered carrier, such as magnesium silicate, silica, carbon, alumina and the like, preferably magnesium silicate, at atmospheric pressure with complete safety in as much as any explosive tendency of the overall system is obviated by the inert carrier. The carrier may be prepared in powder form from magnesium silicate having a bulk density of about 0.2 to 1.0 gram/centimeter. A solution of a copper salt, and optionally a bismuth compound are added to the carrier; the bismuth compound inhibits the polymerization of acetylene by copper oxide. The mixture is dried and then calcined to convert the salts to the oxide precursor of the active catalyst.

Currently, BASF markets a Reppe reaction catalyst prepared by the coprecipitation of copper and bismuth nitrates using sodium carbonate, in the presence of a magnesium silicate carrier, in an attempt to coat the carrier particles with the copper and bismuth carbonates and, thus, present a large surface area of copper-containing catalyst. The magnesium silicate is in the form of small spheres with a particle size $d_{50}$ of about 10 to 20 microns. However, it has been found that when the catalyst is prepared this way, most of the copper and bismuth oxides do not coat the magnesium silicate spheres, and these oxides are present as separate particles not associated with the carrier. While catalysis is maintained, the separate particles are disadvantageous during reaction processing, which involves a filtration step.

SUMMARY OF THE INVENTION

The object of this invention is to obtain a Reppe reaction catalyst that contains copper oxide, optionally, bismuth oxide, and a siliceous carrier so that the copper oxide and bismuth oxide are effectively coated around the particle and are not predominantly separate entities. It is also an object of this invention that the catalyst made with such a coating of copper and bismuth oxides is more active for the ethynylation of formaldehyde to make 1,4 butynediol than the catalyst where the coating is poor or nonexistent.

In accordance with the present invention, a method of preparing a superior ethynylation catalyst is provided so that the copper oxide and, optionally, bismuth oxide coat the carrier particles in a substantially complete manner, so as to yield a core-shell catalyst where the core is a siliceous material and the shell is a mixture of copper oxide and bismuth oxide. The invention relates to using the approach of deposition precipitation, in which the copper and bismuth are precipitated on the support spheres using sodium hydroxide instead of sodium carbonate. The use of NaOH allows the siliceous surface to be populated with hydroxyls which are precursors of surface O anions. Such a surface reacts with Cu and Bi cations leading to a good coating of Cu and Bi entities.

DETAILED DESCRIPTION OF THE INVENTION

Preparation of the Catalyst

Figure 1:
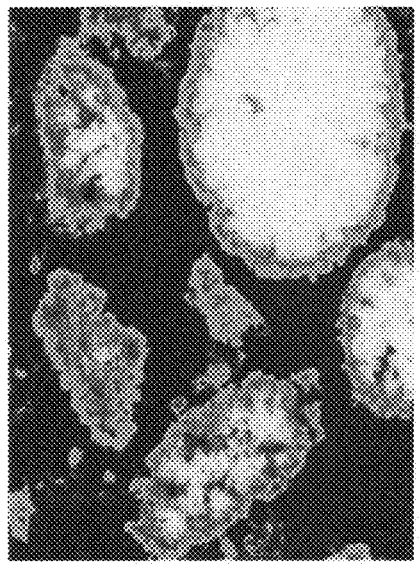
FIG. 1 is an image of the inventive catalyst using Scanning Electron Microscopy coupled with Energy-Dispersive Spectroscopy (SEM-EDS).

The siliceous particles generally will have an average diameter of from about 5 to 60 microns, preferably from about 10 to 30 microns. The carrier particles are first added to water in a precipitation vessel. An acidic solution is made up of a water soluble copper salt or a mixture of copper and bismuth salts in a separate vessel. A non-limiting example of a particularly useful water soluble salt is the nitrate salt. A basic solution is made up with NaOH also in a separate vessel. The temperature of the solutions are set at the precipitation temperature which is held constant throughout the precipitation process with a value anywhere from about 30° C. to about 90° C. The acid mixture and the sodium hydroxide solution are simultaneously added to the vessel containing water and the siliceous carrier particles. This simultaneous addition of the two streams is to ensure consistency in the precipitation of the hydroxides and the proper coating of the support. The precipitation is carried out at a constant pH of about 6 to about 10. During precipitation, the flow of the acid solution is kept constant while the flow of the NaOH solution is adjusted to keep the precipitation pH constant. The time of precipitation may be anywhere from 15 mins to 120 mins. Usually the time is about 60 mins to about 90 mins. After the precipitation step, the precipitate may be aged for a short time, about 15 mins to about 120 mins; although it has been found that it is not imperative to age the precipitate in order to make a good catalyst. The precipitate is filtered, washed, and dried. The dried material is calcined in air. The calcination temperature may vary between 250 to about 550° C.

Catalyst Composition

The catalyst comprises from about 30 to about 60 wt %, preferably 40 to about 50 wt % cupric oxide, and, optionally, from about 1.0 to about 5 wt %, preferably, about 2 to 4 wt % bismuth oxide. Sodium levels as $Na_2O$ may be from about 0.5 to about 3 wt %. The siliceous carrier particles can be silica or metal silicates, such as Group II and III metal silicates, including clays which include aluminum silicates. A particularly useful carrier material is magnesium silicate. Magnesium silicate can be obtained from PQ Corporation, under the commercial tradename of Britesorb AMS500. This commercial product has a $d_{50}$ particle size of about 15 microns. Britesorb AMS600 with a slightly larger $d_{50}$ of about 25 microns is also useful. These commercial materials contain about 77 wt % silica, about 20 wt % MgO, and about 3 wt % $Na_2O$. Impurities in small amounts such as alumina may be present. Other magnesium silicate materials with different compositions may be used. Support carriers with only silica and without other metals may also be used effectively.

Ethynylation Process

Ethynylation processes vary from practitioner to practitioner. It is believed that the catalyst of this invention is applicable to all specific types of ethynylation processes. For example, an ethynylation process using the catalyst of this invention can be that as described in afore-mentioned U.S. Pat. No. 3,920,759. The catalyst of this invention is not to be limited by the description of the process of using same, as described herein.

Accordingly, as described in U.S. Pat. No. 3,920,759, the active catalyst is preferably generated by means of the introduction of the acetylene into the formaldehyde-catalyst reaction medium.

As stated, when generating the catalyst, the cupric precursor in situ is subjected to the simultaneous action of the reactants at the required pressure in a substantially aqueous medium at the temperature of about 60° to 120° C. At temperatures substantially outside this range, or in strongly basic or acidic media, or acetylene partial pressures greater than 2 atmospheres, or in the substantial absence of either formaldehyde or acetylene, poor catalyst tends to result. Preferably, the catalyst generation temperature is in range of 60° to 120° C. The pH of the aqueous medium is in the range of 3 to 10, and preferably 5 to 6. The concentration of formaldehyde in the aqueous medium is ordinarily in the range of 5 to 60, advantageously at least 10 and preferably 30 to 40 weight % at the outset of the reaction.

Ordinarily, the partial pressure of acetylene over the aqueous medium is in the range of 0.1 to 1.9 atmospheres; preferably it is in the range of 0.4 to 1.5.

In carrying out the catalyst generation, nitrogen or another substantially inert gas such as methane or carbon dioxide may be present, as may also the common components of crude acetylene, such as methyl acetylene and ethylene. Oxygen is preferably excluded for safety reasons. In small catalyst batches, the supported cupric precursor may be slurried in cold neutral formaldehyde solution and the acetylene introduced as the slurry is heated. Equivalent results are obtained by heating the catalyst slurry with formaldehyde at not too high a temperature, such as 70° C., for a period of several hours before introducing acetylene. For larger batches, it may be preferable to introduce the cupric precursor incrementally to a hot neutral formaldehyde solution under acetylene pressure. The aqueous solution may advantageously be a stream containing propargyl alcohol and/or butynediol, e.g., a recycle stream.

The catalyst generation reaction is preferably continued until the cupric copper is substantially completely converted to cuprous copper form, which with the preferred cupric precursors, generally requires 4 to 48 hours after all the precursor has been contacted under the prescribed conditions. Preferably, also, the prescribed conditions of temperature, pH and acetylene/formaldehyde concentration balance and range will be maintained throughout the catalyst generation. However, departures from the prescribed conditions during the course of the preparation reaction can be tolerated, as the reaction is relatively insensitive to minor changes in operating conditions.

The pH of the aqueous medium normally decreases as the reaction proceeds, at a rate and to an extent, which tends to increase with the initial acidity of the reaction medium and also with the reaction temperature. Accordingly, the pH may be, and advantageously is, controlled to some extent by beginning at the preferred initial pH of 3 to 10, to some extent by operating in the preferred temperature range of 60° to 120° C. Additional control may be achieved by adding small amounts of acid acceptor such as sodium acetate as the reaction proceeds. Further control may be achieved by carrying out the catalyst generation as a continuous stirred reaction, fresh neutral formaldehyde solution being continuously introduced into an agitated reaction zone, (any acidic effluent may, if desired, be filtered away from the copper-containing particles) as the reaction proceeds, all the while maintaining the acetylene partial pressure.

The ethynylation reaction per se, comprises contacting the reactants at a partial pressure of not more than about 1.9 atmospheres with an aqueous slurry of the catalyst as above described, in a continuous stirred reaction at 80° to 120° C. The formaldehyde and acetylene are preferably continuously fed into the reaction zone where they are introduced into and preferably below the surface of, the aqueous catalyst slurry, and thoroughly mixed into the same by vigorous agitation, and effluent is continuously withdrawn.

The reaction temperature for ethynylation is desirably 60° to 120° C., advantageously 80° to 115° C., and preferably 85° to 110° C. Advantageously, the pH of the reaction mixture will be in the 3 to 10 and preferably 4.5 to 7 range, and may be maintained by ion exchange or acid acceptor treatment of the continuous feed or by addition of a suitable buffering agent.

The formaldehyde concentration in the liquid medium in contact with the slurried catalyst in the course of the ethynylation reaction will ordinarily be 0.5 to 60%, and advantageously at least 0.5 to 37% under steady state conditions. The acetylene partial pressure will ordinarily be at least 0.5 atmospheres. Advantageously, the acetylene partial pressure will be in the range of 0.4 to 1.9 atmospheres. Preferably, the acetylene partial pressure above the aqueous medium will be 0.5 to 1.5 atmosphere and the catalyst will be present in amounts of about 1 to 20 weight parts per 100 weight parts of aqueous medium. For the purpose of the present invention, in the substantial absence of extraneous gas, the acetylene partial pressure may be taken as the total pressure minus the absolute pressure of water and formaldehyde at the reaction temperature. As in the catalyst generation, crude acetylene may be used, but for safety reasons it should be advantageously substantially free of oxygen.

The effluent from the reaction zone may be heated and/or subjected to reduced pressure to volatilize formaldehyde, propargyl alcohol and a portion of the water which are condensed and combined with supplemental concentrated formaldehyde for recycle to the ethynylation reactor, purging any buildup of methanol at convenient intervals in a continuous operation, and sending the balance of effluent as aqueous alkynol directly to hydrogenation. Alternatively, effluent from the reaction zone may be fed to a conventional plug flow ethynylation to react any excess formaldehyde.

The invention will be more specifically described and explained by means of the following examples, which are not to be considered as limiting but merely illustrative of the invention. All parts and proportions therein as well as in the appended claims are by weight unless otherwise specified.

Example

A catalyst (CATALYST 1) of the invention was prepared with the reagents noted in Table 1.

TABLE 1

| Reagents | Amounts |
| --- | --- |
| 16 wt % Copper nitrate solution as Cu, g | 1087 |
| 22.3 wt % Bismuth nitrate solution as Bi, g | 28.5 |
| Britesorb AMS500, g as is | 347.9 |
| (23 wt % LOI associated with it) | |
| Water heel, g | 1316.5 |
| 15 wt % NaOH, g (typically 90 to 95% used) | 1600 |

| Catalyst Analyses, VF | Wt % |
| --- | --- |
| CuO | 47 |
| $Bi_2O_3$ | 2 |
| $SiO_2$ | 40 |
| MgO | 10 |
| $Na_2O$ | 0.6 |
| $Al_2O_3$ | 0.5 |

The catalyst was prepared as noted in the section above. The temperature of precipitation was 50° C. and the pH of precipitation was kept constant at 8.5. The catalyst was tested for initial activity for the consumption of formaldehyde.

Catalyst Testing Procedure

Testing was carried out in two steps. First the catalyst was activated to form the active copper acetylide. It was then transferred to the reaction vessel.

Activation

Catalyst activation was carried out in a 4-port quartz reactor flask containing 100 cc formalin (37 wt % formaldehyde in water). The pH of the formalin was initially adjusted to about 8 by adding 1.5 M NaOH. The neat formalin is acidic (pH=3 to 4) due to formic acid impurities. This acid must be neutralized prior to contacting the catalyst with formalin or the copper in the catalyst may form copper formates and dissolve in solution. Next, 15 g of catalyst were added to the pH adjusted formalin. The flask was purged with nitrogen, stirring was started, and acetylene was introduced at 50 cc/min to the catalyst—formalin slurry at room temperature. The flask was then lowered into a recirculating water bath and heated to 80° C. This procedure forms the active Cu(I) acetylide species [$Cu_2C_2$].

The formic acid produced in this step was continuously neutralized by adding 1.5 M NaOH to the slurry, thus keeping the pH at about 8. After 5 hours, the reactor was cooled to room temperature under flowing acetylene. Once it reached room temperature, acetylene was purged from the flask with nitrogen, the reactor was disassembled, and the slurry removed. It was weighed, centrifuged, and decanted, leaving wet catalyst ready for activity testing.

Reaction

Reaction studies were carried out using 0.5 g of the activated catalyst (dry basis) loaded into a stainless steel stirred autoclave containing 45 cc formalin. As with the activation procedure, the pH of the formalin was initially adjusted to about 8. The reactor was purged with nitrogen and acetylene before starting the reaction. The reactor was operated in a semi-batch fashion while stirring at 1450 RPM. At the start, acetylene from pressurized ballast cylinders was introduced to the reactor through a pressure regulator set at 15 psig (the reaction pressure), and the reactor was heated at approximately 2° per min to 80° C. NOTE: the reactor should not be heated in the absence of acetylene or the Cu acetylides will reduce to $Cu^0$, thus deactivating the catalyst. As the reaction progressed, acetylene uptake was monitored via pressure changes in the ballast cylinders. After 5 hours, the reactor was cooled in flowing acetylene and subsequently purged with nitrogen. The slurry was removed, centrifuged, and decanted. The product mixture was analyzed by gas chromatography in which butynediol (primary product) and propargyl alcohol (product intermediate) were quantified. Because formaldehyde is invisible to GC analysis, a sodium sulfite titration method was used to determine the amount of formaldehyde remaining in the product. Thus, overall formaldehyde conversion was calculated based on 300 min reaction time and 0.5 g catalyst; and the initial catalytic reaction rate in terms of kg formaldehyde converted per kg of catalyst per hour was calculated.

Activity Comparison

A comparison of the initial activity of CATALYST 1 (the inventive catalyst) was made with a commercial BASF catalyst Cu5020P which has very similar copper and bismuth content. Conditions are given in the "catalyst testing procedure" section.

TABLE 2

| | % Formaldehyde conversion | Rate, kg/kg catalyst/h |
| --- | --- | --- |
| CATALYST 1 | 11.3 | 0.82 |
| Commercial catalyst | 7.7 | 0.56 |

Characterization of the Catalyst

Figure 2:
FIG. 2 is an image of the prior art catalyst using Scanning Electron Microscopy coupled with Energy-Dispersive Spectroscopy (SEM-EDS).
Figure 3:
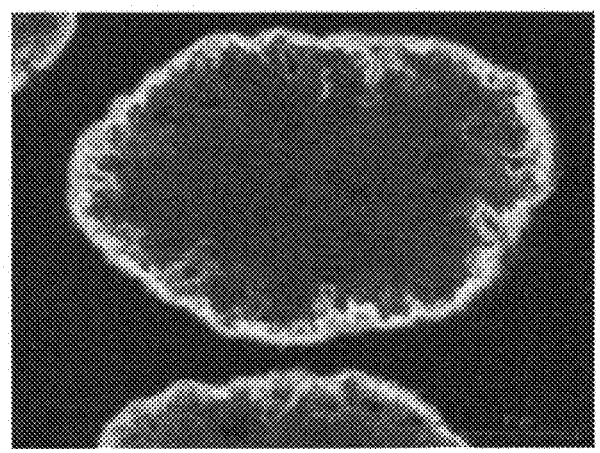
FIG. 3 is an SEM image at a higher resolution of the inventive catalyst.

In order to note the coverage of Cu and Bi oxides around the magnesium silicate spheres, Scanning Electron Microscopy coupled with Energy-Dispersive Spectroscopy (SEM-EDS) was used. FIGS. 1 and 2 show images of catalyst 1 and the prior art catalyst prepared with a sodium carbonate precipitation, respectively (laboratory preparations). The white portion of the catalyst shows the magnesium silicate carrier, whereas the gray color indicates the copper and bismuth oxides. As can be seen from FIG. 1, the copper and bismuth oxides form a coating around the carrier particle, whereas in FIG. 2, the copper and bismuth oxides are particles separate from the magnesium silicate carrier. The higher magnification SEM image (FIG. 3) shows a commercially prepared catalyst equivalent to catalyst 1. The tight uniform shell of Cu and Bi oxides covering the magnesium silicate sphere can be seen as a grayish color around the dark carrier particles.

The invention claimed is:

1. A method of preparing a catalyst for the ethynylation of formaldehyde which comprises: depositing by precipitation copper hydroxide via the reaction of an acidic copper salt solution with an alkaline metal hydroxide, on a particulate siliceous carrier, and calcining the treated carrier to yield a copper oxide coating around said particulate siliceous carrier, wherein said alkaline metal hydroxide is provided in a separate vessel from said acidic solution, and said siliceous carrier particles are provided in water in a precipitation vessel separate from said alkaline metal hydroxide and said acidic copper salt solution.

2. The method of claim 1, wherein a mixture of copper and bismuth hydroxides are deposited on said carrier.

3. The method of claim 1, wherein said acidic solution is made of a mixture of copper nitrate and bismuth nitrate.

4. The method of claim 1, wherein said alkali metal hydroxide is sodium hydroxide.

5. The method of claim 4, wherein said acidic solution and said sodium hydroxide are added simultaneously to the precipitation vessel.

6. The method of claim 1, wherein said precipitation is carried out at a constant pH of between about 6 to about 10.

7. The method of claim 1, wherein said precipitation is carried out at a contrast pH of between 7.5 to 9.5.

8. The method of claim 1, wherein said precipitation is carried out at a temperature of about 40° C. to 90° C.

9. The method of claim 8, wherein said temperature is between 45° C. to 65° C.

10. The method of claim 1, wherein said precipitate is filtered, washed and dried and the dried material calcined in air at a temperature between about 250 to about 550° C.

11. The method of claim 1, wherein said siliceous carrier particles comprise silica.

12. The method of claim 1, wherein said siliceous carrier particles comprise a metal silicate.

13. The method of claim 1, wherein said siliceous carrier particles comprise a magnesium silicate.

14. A novel ethynylation catalyst comprising the product formed by the process of claim 2.

15. The catalyst of claim 14, comprising 30 to about 60 wt. % cupric oxide and from about 1.0 to about 5 wt. % bismuth oxide.

16. The catalyst of claim 14, comprising 40 to about 50 wt. % cupric oxide and from 2 to 4 wt. % bismuth oxide.

17. The catalyst of claim 14, wherein said carrier comprises magnesium silicate.

18. The catalyst of claim 17, wherein said magnesium silicate has an average diameter of 5 to 60 microns.

19. The catalyst of claim 17, wherein said magnesium silicate has a particle size of about 10 to 30 microns.

20. The catalytic ethynylation of formaldehyde with acetylene, the Reppe reaction, conducted in the presence of said catalyst of claim 14.

* * * * *